US010202634B2

(12) United States Patent
Baasner et al.

(10) Patent No.: US 10,202,634 B2
(45) Date of Patent: Feb. 12, 2019

(54) DETECTION OF STARCH LEVELS IN BIOLOGICAL MATRICES

(71) Applicant: FRESENIUS KABI DEUTSCHLAND GMBH, Bad Homburg (DE)

(72) Inventors: Silke Baasner, Schöneck (DE); Frank Nocken, Frankfurt (DE); Klaus Biemel, Saarbrücken (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 44 days.

(21) Appl. No.: 15/381,560

(22) Filed: Dec. 16, 2016

(65) Prior Publication Data

US 2017/0175165 A1    Jun. 22, 2017

(30) Foreign Application Priority Data

Dec. 17, 2015  (EP) .................................. 15200822

(51) Int. Cl.
    *C12Q 1/40*    (2006.01)
(52) U.S. Cl.
    CPC ........... *C12Q 1/40* (2013.01); *G01N 2560/00* (2013.01)
(58) Field of Classification Search
    CPC ... C12Q 1/40; C12Q 1/00; C12N 9/16; C12N 9/2408; C12N 9/2414; C12N 9/2425; C12N 9/2428; C12N 9/96; C12N 15/8218; C12N 15/8247; C12N 9/1241; C12N 9/14; A61K 3/00; Y02E 50/16; Y02E 50/17; C07K 14/415; C12Y 207/07027; C12Y 306/03; C12Y 302/01001; G01N 2560/00; A23L 29/212; A23L 29/35; C12P 19/14
    See application file for complete search history.

(56) References Cited

U.S. PATENT DOCUMENTS 3,937,821 A      2/1976  Irikura et al.
2006/0246513 A1* 11/2006  Bohannon .............. G01N 33/53
                                                 435/7.1

FOREIGN PATENT DOCUMENTS

WO    2002/035212   5/2002
WO    2012/122255   9/2012

OTHER PUBLICATIONS

Avois, et al."Rapid screening of HES in urine with colorimetric detection," Reprint: Recent Advances in Doping Analysis (12), *Sport und Buch Strauβ* (2004), 371-376.
Behne, et al. "The pharmacokinetics of acetyl starch as a plasma volume expander in patients undergoing elective surgery," *Anesthesia & Analgesia* 86.4 (1998), 856-860.
Esposito, et al. "Investigation of urinary excretion of hydroxyethyl starch and dextran by UHPLC-HRMS in different acquisition modes," *Biol. Sport* 31 (2014), 95-104.
Jungheinrich et al. "The pharmacokinetics and tolerability of an intravenous infusion of the new hydroxyethyl starch 130/0.4 (6%, 500 mL) in mild-to-severe renal impairment," *Anesthesia & Analgesia* 95.3 (2002), 544-551.
Lesch, "Hydroxyethylstärke (HES) im Urin nach Mehrfachinfusion von HES (450/0, 7): physiko-chemische Veränderungen der Substanzcharakteristika einer hochsubstituierten, hochmolekularen HES," (2004), 1-98.
Leuschner et al. "Tissue storage of 14C-labelled hydroxyethyl starch (HES) 130/0.4 and HES 200/0.5 after repeated intravenous administration to rats," *Drugs in R & D* 4.6 (2003), 331-338.
Otto et al. "A method for detection and quantification of hydroxyethyl starch in plasma," *Critical Care* 16.3 (2012), 426.
Schaeffer et al. "Preparation and high-performance size-exclusion chromatographic (HPSEC) analysis of fluorescein isothiocyanate-hydroxyethyl starch: macromolecular probes of the blood-lymph barrier," *Microvascular Research* 32.2 (1986), 230-243.
Schramm et al. "Impact of the C2/C6 ratio of high-molecular-weight hydroxyethyl starch on pharmacokinetics and blood coagulation in pigs," *The Journal of the American Society of Anesthesiologists* 107.3 (2007), 442-451.
Sirtl et al. "Tissue deposits of hydroxyethyl starch (HES): dose-dependent and time-related." *British Journal of Anaesthesia* 82.4 (1999), 510-515.
Ständer et al. "Differential storage of hydroxyethyl starch (HES) in the skin: an immunoelectron-microscopical long-term study." *Cell and Tissue Research* 304.2 (2001), 261-269.
Thevis et al. "Nachweis des Plasmavolumenexpanders Hydroxyethylstärke in Humanurin." *Deutsche Zeitschrift für Sportmedizin* 52.11 (2001), 316-320.
Thomas et al. "Measuring blood volume with fluorescent-labeled hydroxyethyl starch." *Critical Care Medicine* 28.3 (2000), 627-631.
Thompson et al. "Intravascular persistence, tissue storage, and excretion of hydroxyethyl starch," *Surgery, Gynecology & Obstetrics* 131.5 (1970), 965-972.
Thyes et al. "Effect of high-and low-molecular-weight low-substituted hydroxyethyl starch on blood coagulation during acute normovolemic hemodilution in pigs." *The Journal of the American Society of Anesthesiologists* 105.6 (2006), 1228-1237.
Yamakage et al. "Pharmacokinetics and safety of 6% hydroxyethyl starch 130/0.4 in healthy male volunteers of Japanese ethnicity after single infusion of 500 ml solution," *Journal of Anesthesia* 26.6 (2012), 851-857.

(Continued)

*Primary Examiner* — Deborah K Ware
(74) *Attorney, Agent, or Firm* — Hylton-Rodic Law PLLC

(57) ABSTRACT

Methods for detecting a starch in a sample are provided. The methods include the steps of initially incubating the sample in the presence of an amylase-containing medium and subsequently subjecting the sample to liquid chromatography mass spectrometry (LC-MS) to detect ions characteristic of the starch in the sample. The amylase-containing medium can include an amylase and blood plasma or the amylase-containing medium can include an amylase and a component selected from the group consisting of about 90-92% water or buffered water, about 8% protein, about 0.9% salt, and/or about 1.1% organic substances. The incubating step can be done in conditions that permit digestion of the starch by the amylase.

19 Claims, 4 Drawing Sheets

(56) References Cited

OTHER PUBLICATIONS

"The World Anti-Doping Code: The 2015 Prohibited List" *World Anti-Doping Agency*. Web. Feb. 14, 2017.
Guddat et al., "Rapid Screening of Polysaccharide-Based Plasma Volume Expanders Dextran and Hydroxyethyl Starch in Human Urine by Liquid Chromatography-Tandem Mass Spectrometry," *Biomedical Chromatography*, vol. 22, No. 7, Jul. 1, 2008, pp. 695-701.
Kolmonen et al., "Specific Screening Method for Dextran and Hydroxyethyl Starch in Human Urine by Size Exclusion Chromatography-in-Source Collision-Induced Dissociation-Time-of-Flight Mass Spectrometry," *Analytical and Bioanalytical Chemistry*, vol. 401, No. 2, Mar. 17, 2011, pp. 563-571.
Wilkes et al., "Hydroxyethyl Starch in Balanced Electrolyte Solution (Hextend)-Pharmacokinetic and Pharmacodynamic Profiles in Healthy Volunteers," *Anesthesia and Analgesia*, vol. 94, No. 3, Mar. 1, 2002, pp. 538-544.
Jurgen H. Gross, "Mass Spectrometry, A Textbook, 2nd Edition", 2011.

\* cited by examiner

DETECTION OF STARCH LEVELS IN BIOLOGICAL MATRICES

CROSS-REFERENCE TO RELATED APPLICATIONS

This U.S. utility application is filed in accordance with 35 U.S.C. § 119(a) and claims the benefit of the filing date of European Application No. 15200822.3, filed Dec. 17, 2015.

FIELD OF THE INVENTION

The present invention is directed to an improved method for the detection of starches, in particular, artificial starches such as hydroxyethyl starch (HES), and to kits for carrying out the method.

BACKGROUND

Hydroxyethyl starches (HESs) are polydisperse, artificial colloids for intravascular volume replacement that are usually derived from the cornstarch amylopectin. HES and HES solutions are highly effective plasma expanders that are particularly useful for the treatment and/or prevention of hypovolemia, acute normovolemic hemodilution, disturbances in capillary blood circulation, as may occur with tinnitus, or the treatment of burns.

The use of HES, however, may lead to its accumulation in plasma and various tissues, and it has been hypothesized that such accumulation may cause unfavorable outcomes, particularly in critically ill patients. In addition, HESs are increasingly misused in sports, especially in high performance endurance sports, even though their use has been banned by the International Olympic Committee (IOC). Therefore, methods for the reliable and sensitive detection of HESs in samples, in particular biological samples, are needed.

Present technologies to measure HESs are either inaccurate, inconvenient and time-consuming, or involve the disadvantageous use of radioactive substances. For example, Leuschner et al. (Drugs R&D 4(6):331-338, 2003) describe the use of a $^{14}C$-labeled HES for the determination of tissue storage of HES after intravenous administration to rats. While this method can be considered the gold standard in terms of sensitivity and accuracy, it is dependent on radiolabeling. Similarly, methods involving fluorescent labelling with fluorescein isothiocyanate (FITC) are known but likewise disadvantageous. Furthermore, methods involving the inconvenient and time consuming precipitation of HES by acetone, acidic hydrolysis and/or additional derivatization steps are known.

An object of the present invention, therefore, is the provision of an improved method for the detection of starches in a sample that is more reliable, quick and convenient, as well as more accurate and sensitive than the previously known methods and does not rely on the use of radioactive substances or other labeling. More particularly, the object of the present invention is the provision of such an improved method that allows the detection of starches in a biological sample that has been isolated from an organism and is used "as is", i.e. untreated and in particular without any preceding precipitation steps.

SUMMARY OF THE INVENTION

The object described above is solved by the methods of this invention as described herein and provided in independent claim 1, which covers a method of detecting a starch in a sample. The method can include the steps of (a) incubating the sample in the presence of an amylase; and (b) subjecting the sample to liquid chromatography mass spectrometry (LC-MS) to detect ions characteristic of the starch in the sample. Advantageous further embodiments are given in the claims dependent thereon.

The present invention is based, at least in part, on the surprising finding that incubating a sample (as described further below) comprising the starch to be detected in the presence of an amylase or amylase-containing medium (e.g., HES) leads to both a significantly improved sensitivity and accuracy of the subsequent LC-MS. In particular, and as will be detailed below, the method of the invention appears to be in no way inferior to the present gold standard in terms of sensitivity and accuracy while no use of radioactive labels is required. In addition, the method of the present invention enables the detection of a starch in a sample without prior treatment of the sample, in particular, without any kind of precipitation and/or derivatization steps. In any embodiment, the sample may be one suspected of including a starch (whether naturally occurring or not) that may have been administered (e.g., administered intravenously) to a subject, and any of the methods can include a step of selecting a subject to be tested and/or selecting, from the subject, a sample type to be tested. "Incubating" the sample with an amylase or amylase-containing medium refers to exposing the sample to the amylase or amylase-containing medium for a time and under conditions that would permit the amylase to hydrolyze to the starch. The hydrolysis may be complete (e.g., the result may be single sugar (e.g., glucose) units) or partial.

The detection of the starch in the sample can comprise detecting the presence of the starch or determining the amount and/or the concentration of the starch in the sample. Furthermore, the ions detected in the present methods are preferably generated during the LC-MS step and are protonated ions.

As described above, the sample used in the present invention need not be treated in a prior step, i.e. the sample preferably is an (otherwise) untreated sample or is used in the present method "as is", for example directly after isolation from an organism and without any further treatment. More preferably, no precipitation steps, no precipitation steps involving acetone, no acidic hydrolysis and/or no derivatization steps may have been applied to the sample.

As an incubation of the sample in the presence of an amylasecan be a step carried out in the present methods, the methods may preferably comprise adding an amylase or amylase-containing medium to the sample prior to the incubation step. More preferably, the step of adding the amylase to the sample can be the first substantive step of the methods of the invention. The amylase can be added to the sample in any suitable way. Preferably, the amylase is added in a solution, more preferably within an aqueous and/or buffered solution. Most preferably, the amylase is added to the sample by the addition of blood plasma. Surprisingly, it has been found that such addition of plasma, which comprises α-amylase, among others, reproducibly led to superior results in the detection of ions characteristic of the starch in the sample. Without wishing to be bound to a specific theory, the inventors believe these improved results in terms of the sensitivity and accuracy of the detection are due to one or more of the various further constituents of plasma.

A composition containing an amylase may be referred to herein as an "amylase-containing medium," which encompasses solid (e.g., powdered, dehydrated, or lyophilized formulations) and liquid compositions. The composition can be, or can include, one or more naturally occurring amylases (an α-, β-, or γ-amylase or any combination thereof), a naturally occurring source of an amylase (e.g., blood, blood plasma, or saliva), a synthetic or recombinantly produced amylase, or a biologically active variant of any of these amylases. The "biologically active variant" can be a fragment or other variant of an amylase that retains the ability to hydrolyze a glycosidic bond (e.g., such as in starch or a HES). The variant may or may not exhibit the same kinetics as its naturally occurring counterpart; it need only be active enough to serve in the present methods. Naturally occurring amylases may be isolated, if desired, for use in the present methods from a human or other mammal that produces an amylase or from an amylase-expressing plant to (including the seeds), fungus (e.g., ascomycetes or basidiomycetes), or bacteria (e.g., *Bacillus*). As indicated above, the amylase or biologically active variant thereof may also be recombinantly produced using expression systems well known in the art. We may not use the term "amylase or an amylase-containing medium" at every opportunity. Unless the context clearly indicates otherwise, it is to be understood that where an amylase can be used, an amylase-containing medium can also be used, and vice versa.

As noted above, plasma may be used as an amylase-containing medium, as may compositions that include any subset or combination of the moieties within plasma. For example, the amylase-containing medium may include one or more of: an amylase (including an α-, β-, or γ-amylase), a salt or electrolytes derived therefrom (e.g., sodium, potassium, calcium, carbonate, phosphate or any combination thereof), a protein other than amylase (e.g., an albumin, a globulin (e.g., an α1, α2, β1, β2, and/or γ-globulin), fibrinogen, a proteolytic enzyme, a protease inhibitor, or a carrier protein, a hormone, a cytokine, and/or an immunoglobulin), an inorganic compound (e.g., iodine, iron, or nonprotein sulphur) and/or a sugar.

Further, the amylase-containing medium may differ from naturally occurring plasma but have about the same aqueous (e.g., water or buffered water) content (about 90-92%), protein content (about 8%), salt content (about 0.9% salt) and/or content of organic substances (about 1.1%) as plasma.

The sample may preferably be a biological sample and may more preferably be obtained from the subject to whom the starch that is to be detected was administered prior to taking of the sample. Any sample, including especially those that may coagulate, can include an anticoagulant, such as citrate, EDTA, heparin or a salt thereof (e.g., an ammonium salt (e.g., ammonium heparin), a lithium salt (e.g., lithium heparin), or a sodium salt (e.g., sodium heparin)). Heparin may be the preferred anticoagulant when a sample includes whole blood or plasma, as it has minimal chelating properties, minimal effects on water shifts, and relative low cation concentrations. Lithium heparin may be preferred as it may be the least likely to interfere with tests for other ions; lithium heparin is essentially free of extraneous ions.

In preferred embodiments, the subject may be an athlete and/or the method may be a method for doping analysis in any competitive or athletic endeavor, or the subject may be a patient, preferably a patient in need of administration of the starch to be detected (e.g., an HES). In the latter case the method may be a method for the determination of the presence, the amount, and/or the concentration of the starch in a patient. The methods of the present invention may preferably be forensic methods, especially in case of the sample being a tissue sample as described below.

Sirtl et al. described that, at least in skin tissue samples, certain HES types could be detected up to 53 months after the HES was administered to the person (Sirtl et al., *Br. J. Anaesth.* 82(4):510-515, 1999). With the methods described here, HES can be detected a minute after it has been administered intravenously and for approximately two years afterward. Accordingly, the invention features methods of determining whether a starch (e.g., HES) has been administered to a subject, and that subject can be a human athlete or any other mammal that is raced or otherwise competes in a sporting event (e.g., a mammal such as a horse or a dog). The methods can more broadly be described as tests to determine whether a subject has been exposed to performance enhancing substances and can include an analysis as described herein for a starch (e.g., HES) as well as tests for other substances such as erythropoietin (EPO). The presence of HES and/or such other substances (particularly where banned) would indicate an attempt to unfairly enhance performance. The subject can also be a patient who has experienced a trauma in which blood is lost (e.g., an extensive surgical procedure or traumatic accident), a burn, or any other condition that results in hypovolemia or for which a volume expander such as VOLUVEN® (6% hydroxyethyl starch 130/0.4 in 0.9% sodium chloride) is prescribed.

In a further embodiment, the starch is administered to the subject ≥about 5 min and ≤about 2 years, preferably ≥about 10 min and ≤about 6 months, preferably ≥about 10 min and ≤about 52 days, more preferably ≥about 10 min and ≤about 30 days, more preferably ≥about 10 min and ≤about 48 h, even more preferably ≥about 10 min and ≤about 24 h, and most preferably ≥about 1 h and ≤about 9 h prior to the taking of the sample. In case of multiple administrations of the starch to the subject, the time intervals given above preferably refer to the last administration of the starch to the subject. The present methods can be repeated over time, at regular intervals (e.g., about every 2, 4, 6, 12, or 24 hours) or random intervals (e.g., as may be called for by an attending physician). More specifically, two or more samples can be obtained from the subject over time and analyzed by the present methods in order to monitor for the accumulation of a starch in the subject.

The methods according to the present invention may be ex vivo methods (i.e., the taking of the sample may not be a part of the method). On the other hand, the methods according to the invention, in any embodiment, can also include a step of identifying a subject to be tested (by virtue, for example, of suspicion that the subject has taken or been given one or more doses of HES or a concern regarding the amount or concentration of HES in the subject's body) and/or a step of providing (e.g., obtaining) a sample (e.g., a bodily tissue, fluid, or feces) from a subject.

The sample may be or may comprise tissue, a body fluid, and/or feces. The term body fluid comprises urine as well as blood and saliva. Preferably, the body fluid sample is a urine sample or a blood sample. It is especially preferred that the sample is urine. In another preferred embodiment, the sample is a blood sample. In any embodiment, the sample can be a sample derived from a human individual.

In further preferred embodiments, the sample is or comprises tissue, urine and/or feces, more preferably tissue and/or urine. The tissue may be tissue from an organ. For example, the tissue may be taken from the skin, kidney or other tissue within the urinary system (e.g., the urinary bladder), liver, spleen, mesenteric lymph nodes, bone marrow, heart, and/or lung. Preferably, it is selected from skin, kidney, heart, urinary bladder and/or liver. Even more preferably, it is selected from an excretion organ (urinary bladder, kidney and/or liver). The skin sample may comprise hair and/or nail or the sample may be a sample of hair or a nail excluding the skin.

In further preferred embodiments, particularly where the sample comprises a tissue or feces, the sample can be homogenized and/or be a solution comprising the homogenized tissue or feces. Such a homogenization step is preferably carried out before the addition of an amylase or amylase-comprising liquid and/or the incubation of the sample.

The homogenate may preferably be diluted prior to incubation. More preferably, the homogenate is diluted in a buffer and/or diluted 1:2 (one part homogenate and two parts buffer). Such a 1:2 dilution of the homogenate prior to the digestion step advantageously yielded an improved detection of the starch. Even more preferably, the buffer used for the dilution is phosphate buffered saline (PBS), most preferably the buffer is PBS without $Ca^{2+}$ and $Mg^{2+}$ and has a pH of 7.4 or about 7.4.

The starch subjected to a method described herein can be any starch that can be digested by an amylase under, for example, one or more of the conditions set out herein or a method known in the art. In preferred embodiments, the starch is an artificial starch, i.e. a starch that is not naturally occurring. Preferably, the (artificial) starch is not endogenously present in the living organism and/or the subject from which the sample was derived.

An artificial starch subjected to a method described herein can be a modified starch, preferably a starch modified by a chemical treatment, even more preferably by a chemical treatment with ethylene oxide. Preferably, the starch is a hydroxyethyl starch (HES). Furthermore, the starch preferably is an unlabeled starch and, in particular, is not labeled radioactively or fluorescently.

The HES can be any suitable HES and typically has an average molecular weight of around 50 kDa to around 700 kDa, more preferably ≥about 70 kDa and ≤about 670 kDa, even more preferably ≥about 130 kDa and ≤about 450 kDa, ≥about 130 kDa and ≤about 260, or ≥about 130 kDa and ≤about 200 kDa. Furthermore, the preferred degree of molar substitution of the HES, i.e. the molar substitution of hydroxyethyl groups per glucose subunit, of the HES detected according to the present methodsis ≥about 0.35 and ≤about 0.80, more preferably it is ≥about 0.4 and ≤about 0.75, ≥about 0.45 and ≤about 0.7, or ≥about 0.5 and ≤about 0.62. For example, HES 130/0.4, commercially available from Fresenius Kabi (VOLUVEN®), is a hydroxyethyl starch with an average molecular weight of 130 kDa and a molar substitution of hydroxyethyl groups per glucose subunit of 0.4.

In various embodiments, the starch detected is HES 670/0.75, HES 450/0.7, HES 260/0.45, HES 200/0.62, HES 200/0.5, HES 70/0.5, and/or HES 130/0.4. Most preferably, the starch is HES 130/0.4.

LC-MS is an analytical technique known to the skilled person that combines the physical separation capabilities of liquid chromatography with the mass analysis capabilities of mass spectrometry. An overview and more detailed explanation of LC-MS and its various variants can be found in Jürgen H. Gross, "Mass Spectrometry, A Textbook, 2nd Edition", 2011, and other scientific literature.

In the present methods, any suitable LC-MS method can be used for the detection of the characteristic ions of the starch. Preferably, the LC-MS is a high resolution LC-MS (LC-HRMS) and/or tandem LC-MS (LC-MS/MS). More preferably, the technique utilizes electron spray ionization (ESI), most preferably it additionally employs in-source collision-induced dissociation (CID). LC-HRMS/MS utilizing ESI and CID has been shown to provide the most accurate results in the methods of the present invention. Thus, in any of the present methods, the LC-MS can be a high resolution tandem LC-MS (LC-HRMS/MS) with electron spray ionization 30 (ESI) and in-source collision-induced dissociation (CID).

In further preferred embodiments, the ions detected by mass spectrometry have a mass to charge ratio (m/z) of 369, 413, 457, 501, and/or 575. Ions with such mass to charge ratios have been shown to be reliable fragments for the detection of HES.

The amylase can be any amylase suitable for the enzymatic digestion of starch (e.g., an HES) by hydrolysis. Amylases are glycoside hydrolases that act on the glycosidic bonds of the starch.

Preferably, the amylase is an α-amylase (EC 3.2.1.1), β-amylase (EC 3.2.1.2) and/or γ-amylase (EC 3.2.1.3) or a biologically active fragment or variant thereof. α-amylase acts on all α-1,4-glycosidic bonds of the starch. β-amylase catalyzes the hydrolysis of the second α-1,4 glycosidic bond, cleaving off two glucose units (maltose) from the non-reducing end at a time. γ-amylase will cleave α(1-6) glycosidic linkages, as well as the last α(1-4)-glycosidic linkages at the nonreducing end of amylose and amylopectin. Especially in case of β-amylase, the skilled person will realize that the ions to be detected according to the present invention will vary from the ones given above.

More preferably, the amylase is an α-amylase, even more preferably the amylase is an α-amylase contained in blood plasma and/or is added to the sample by addition of blood plasma or another amylase-containing medium. Even more preferably, the amylase, preferably α-amylase, and/or the blood plasma added to the sample is an amylase and/or blood plasma from the same species as the species from which the sample is derived. For example and even more preferred, if the sample is derived from a human, the α-amylase and/or blood plasma is likewise a human amylase and/or human blood plasma. Most preferably, the amylase, preferably α-amylase, and/or the blood plasma added to the sample is an α-amylase and/or blood plasma from the same individual as the individual from whom the sample is derived. For example and preferably, if the sample is derived from a human individual, the α-amylase and/or blood plasma is likewise a human amylase and/or blood plasma from the same individual.

The incubation of the sample can be carried out with any suitable set of parameters that allow the digestion of the starch by the amylase. For example, the sample may be incubated at about room temperature (RT) and for a time of around 120 min (with, for example, plasma containing an amylase or an amylase-containing medium as described herein).

In a further preferred embodiment, the incubation step is preceded by a first dilution step in which an amylase or amylase-containing medium is added to the sample. The term "amylase-containing medium" comprises any suitable liquid comprising an amylase. Without wishing to be bound to a specific theory, the inventors assume that, in combination, the addition of an amylase and a dilution of the sample lead to even better results in terms of the sensitivity and accuracy of the methods of the present invention. More preferably, the first dilution step comprises the dilution of the sample with an amylase-containing medium at a ratio of ≥about 1:1 and ≤about 1:10, more preferably at a ratio of ≥about 1:2 and ≤about 1:8, even more preferably at a ratio of ≥about 1:3 and ≤about 1:5, most preferably at a ratio of about 1:4. The amylase-containing medium preferably is blood plasma, even more preferably blood plasma from the same species as the species from which the sample is derived, and most preferably blood plasma from the same individual from whom the sample is derived.

In a further preferred embodiment, the incubation step is preceded by a second dilution step in addition to the first dilution step. More preferably, the second dilution step comprises the addition of an ethanol/water mixture, more preferably with an ethanol/water ratio of 1:1. Surprisingly, the addition of an ethanol/water mixture further improved the sensitivity and accuracy of the methods of the present invention. More preferably, the volume of the ethanol/water mixture added is ≥about 0.1 to ≤about 3 times the volume of the sample after the first dilution step, and most preferably it is around 0.2 times the volume of the sample after the first dilution step.

Preferably, the sample is incubated at a temperature of ≥about 10° C. and ≤about 50° C., more preferably at a temperature of ≥about 20° C. and ≤about 40° C., and even more preferably at a temperature of ≥about 18° C. and ≤about 25° C. or ≥about 20° C. and ≤about 25° C.

The sample is furthermore preferably incubated in the presence of the amylase for a duration of ≥about 10 min and ≤about 200 min, more preferably ≥about 100 min and ≤about 150 min or ≥about 100 min and ≤about 140 min, and most preferably around 120 min.

The skilled person will appreciate that the concentration of the amylase will have an effect on the speed of the digestion of the starch in the sample. Preferably, the sample is incubated in the presence of an amylase at a concentration of ≥about 1 and ≤about 200 U/l, more preferably ≥about 4 and ≤about 100 U/l, and even more preferably ≥about 4 and ≤about 20 U/l.

In case of HES as a starch and addition of an α-amylase, the sample is preferably incubated at an α-amylase concentration of ≥about 4 and ≤about 20 U/l, a temperature of ≥about 20° C. and ≤about 25° C., and for a duration of ≥about 100 min and ≤about 150 min, more preferably for around 120 min. It could advantageously be shown that in case of HES as a starch and α-amylase as the digesting enzyme, no heating of the sample is required but a digestion at about RT (which generally is in the range of ≥about 20° C. and ≤about 25° C.) yielded optimal results. Likewise, it was demonstrated by a kinetic analysis that an incubation for a duration of ≥about 100 min and ≤about 150 min, more preferably for around 120 min at an α-amylase concentration of ≥about 4 and ≤about 20 U/l yielded the best results.

As will be appreciated by the skilled person, the embodiments described herein (e.g., embodiments in which the present methods are carried out with any of the various sample types described herein under any of the various conditions of time, temperature, concentration, pH, etc. . . . ) may be combined freely as long as not explicitly stated otherwise or as long as such a combination does not lead to an evident inconsistency.

The invention also features kits comprising one or more compositions useful in carrying out the present methods and instructions for use. For example, the kit may include an amylase-containing medium (e.g., in a vial to which a sample can be added) and, optionally, one or more solutions or instruments for obtaining, manipulating, and/or preparing a sample for LC-MS (e.g., LC-HRMS/MS). The kit may further include a composition or material useful in detecting one or more of an anabolic drug, stimulant, ergogenic aid, adaptogen, nootropic, painkiller, sedative, anxiolytic, blood booster or vectors designed for gene doping. Similarly, the methods of the invention may include assessing a starch (e.g., HES) as described herein as well as assessing the sample for the presence of, or amount of, one or more of the performance enhancing agents just listed. The instructions provided with a kit can take the form of, for example, printed material (e.g., an insert), an audio or visual presentation, or instructions for accessing a website or other informative resource.

The parameters of the methods set out herein can vary from a stated reference value (e.g., from a stated ratio, concentration, amount, pH, temperature, or time) by a limited amount. Therefore, it is to be understood that the methods encompass values that are "about" or "around" those specifically provided. These terms ("about" and "around") mean a value that includes an inherent variation of error for the device or the method being employed to determine the value or plus-or-minus 10% of the stated value, whichever is greater.

Further advantages, details and embodiments of the present invention will be described in the following detailed description and examples.

DETAILED DESCRIPTION

Materials and Methods

Figure 1:
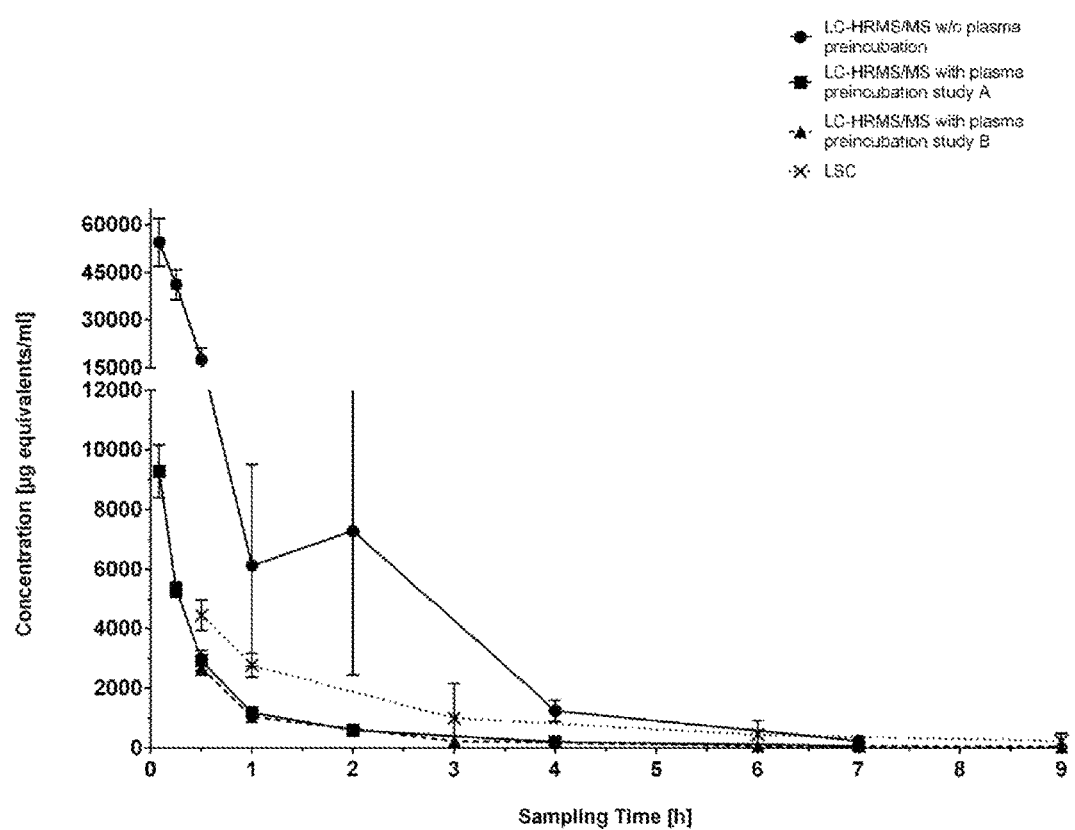
FIG. 1 is a line graph depicting the mean concentration of HES 130/0.4 equivalents/ml) in plasma samples over time (hours) as measured by LC-HRMS/MS without plasma incubation; as measured by LC-HRMS/MS with plasma incubation (study A and study B); and as measured by LSC.

The presence of HES 130/0.4 (Fresenius Kabi) in tissues/organs and feces samples of Sprague Dawley rats was detected. The samples were analyzed by the nonradioactive method LC-HRMS/MS as described below.

For reasons of cross-validation of the sensitivity and accuracy of the method according to the invention, a parallel study was performed with $^{14}$C-radiolabelled HES 130/0.4. The samples arising therefrom were analyzed by quantitative radiochemical analysis.

Preparation of Blank Samples

Blank samples or standards and quality controls for LC-HRMS/MS were derived from untreated rats. Likewise, blank plasma for the incubation of the samples prior to the LC-HRMS/MS was obtained from untreated rats.

Preparation of Samples

Samples were collected from adult male and female Sprague Dawley rats at various times after a 10 min slow bolus injection of 1 g/kg HES 130/0.4 (the volume was 10 ml/kg of a 10% HES 130/0.4 in 0.9% NaCl solution). Samples were collected 30 min, 1 h, 3 h, 6 h, 9 h, and 24 h after treatment. Samples can similarly be obtained from any subject at one or more of these same time intervals to practice the present methods.

Samples were either incubated with blank plasma containing α-amylase and other blood components or were not incubated with blank plasma. Furthermore, the study was repeated (study A and study B). If desired, blank plasma or any other amylase-containing medium can be used as a control in any of the present methods.

Urine samples were collected at given time points if possible. Samples of tissue/whole organs and feces were initially weighed, and the present methods may optionally include a step of weighing or otherwise quantifying a given sample. From each rat, tissue/organs and feces were homogenized and analyzed separately. In the present methods, more than one sample type may be obtained and tested from a given subject. Tissue/organs and feces were homogenized in toto (urinary bladder 1+3, w:v, all other organs and feces 1+2, w:v) in PBS using a Precellys 24/Dual homogenizer in combination with 2.8 mm ceramic beads in 2-ml tubes or 7-ml tubes, depending on the size of the organ to be analyzed. Organs weighing more than 2 g (e.g. liver, kidneys) were cut into smaller pieces with a scalpel blade and divided in more than one 7-ml tube for homogenization. Such division may be made in carrying out any of the present methods, if desired. The contents of the tubes holding separate pieces from one organ were pooled again after homogenization. Materials and implements for sample procurement and treatment (e.g., sectioning and homogenization) may be a part of the kits of the invention.

For the incubated samples, a volume of 10 µl of each sample was diluted with lithium-heparin blank plasma at a 1+4 ratio. A volume of 10 µl ethanol/water (1+1, v:v) was added and the mixture was incubated for 2 hours at ambient temperature (22±2° C.).

HES Quantification by LC-HRMS/MS

All samples were then processed according to the following sample extraction protocol: 50 µl trichloroacetic acid (TCA) 27% (v:v) were added to 40 µl ethanol/water (1+1, v:v; containing the processing control Griseofulvin, 1.875 ng/ml). The mixture was vigorously shaken (5 seconds) and centrifuged for 10 min at 6,000×g and 20° C. An aliquot of the particle free supernatant was transferred to a 200 µl sampler vial and subsequently subjected to LC-HRMS/MS. One or more of these components (e.g., an extraction agent such as TCA or a diluent such as ethanol, water, or a mixture thereof) may be included in the kits of the invention.

For the LC-HRMS, an Accela U-HPLC pump and an Accela autosampler (Thermo Fisher Scientific) connected to a Q-Exactive mass spectrometer (Orbitrap technology with accurate mass) equipped with a heated electrospray (H-ESI 2) interface (Thermo Fisher Scientific, USA) was used. Data handling was performed with the standard software Xcalibur 2.1.

The MS tune file comprised manually adjusted collision induced dissociation (CID) parameters optimized for maximum abundance of desired in source fragmented HES fragments. As lock mass for internal mass calibration the $[M+H]^+$ ion of diisooctyl phthalate (m/z 391.28429) was used, which is ubiquitously present in the environment (solvent system).

The analyzer was run in the MS/MS mode combined with a full scan (200-520 Da). The mass resolution of the Orbitrap was set to 70,000. Further analyzer settings were as follows: max. trap injection time 60 ms, sheath gas 40, aux gas 10, sweep gas 2, spray voltage 4 kV, capillary temperature 350° C., H-ESI-2 heater temperature 350° C.

The HPLC pump flow rate was set to 500 µl/min and analytes were separated on an Aeris Widepore XB-C8, 3.6 u, 50×2.1 mm analytical column (Phenomenex, Germany) with an Aeris Widepore C5 guard cartridge (4×2 mm, Phenomenex, Germany).

Test item concentrations were calculated by multiplication of the concentrations determined in analytical solution by LC-HRMS/MS with the corresponding dilution factors used during sample processing.

Results

Determination of the Concentration of HES in Various Samples

The mean concentration of HES 130/0.4 in various samples was determined according to a method of the invention (LC-HRMS/MS with plasma preincubation) in two separately-conducted experiments (study A and study B).

Furthermore, a comparison of the present methods to two different methods was carried out in order to determine the sensitivity and accuracy of the present methods. In the first comparative method, the same samples were measured by a method in which the incubation step with plasma was omitted (LC-HRMS/MS w/o plasma pre-incubation) but which was otherwise identical to the method of study A and study B. In the second comparative method, the samples were analyzed by liquid scintillation counting (LSC) as e.g. described in Leuschner et al. (*Drugs R&D*, 4(6):331-338, 2003), representing the current "gold standard".

As shown below, an incubation step according to present invention led to significantly improved detection of HES. In particular, sensitivity and accuracy were improved and very closely resembled the results determined by LSC. In contrast, a determination of HES by LC-HRMS/MS that was otherwise identical but omitted the initial incubation step with an amylase led to significantly higher readings as compared to determination by the "gold standard" (LSC).

TABLE 1

| | Concentration in Plasma [µg equivalents/g] | | | |
|---|---|---|---|---|
| Sampling Time [h] | LC-HRMS/MS w/o plasma preincubation | LC-HRMS/MS with plasma preincubation study A | LC-HRMS/MS with plasma preincubation study B | LSC |
| 0.083 | 54479.88 | 9281.39 | | |
| 0.25 | 41237.49 | 5326.07 | | |
| 0.5 | 17580.37 | 2939.97 | 2666.78 | 4857.55 |
| 1 | 6127.93 | 1190.17 | 1052.04 | 3043.24 |
| 2 | 7295.35 | 591.75 | | |
| 3 | | | 239.17 | 1153.85 |
| 4 | 1247.77 | 206.22 | | |
| 6 | | | 74.71 | 470.63 |
| 7 | 240.00 | 75.32 | | |
| 9 | | | 36.31 | 244.74 |
| 24 | | | 2.50 | 38.80 |

The results depicted in Table 1 demonstrate that the method described above (performed in study A and study B) reliably detected the concentration of HES in plasma. In particular, the measured concentrations are in accordance with those determined by LSC. In contrast, the omission of the inventive incubation step leads to a significant deviation from the result obtained by LSC. These results are depicted graphically in FIG. 1.

As plasma samples are readily derivable/obtainable samples and no homogenization of tissue is necessary, the analysis of plasma is especially well suited for detecting the presence of HES in an organism.

Given the excellent and surprising results in detecting HES in plasma samples, the present methods, carried out using plasma samples, may especially be used in clinical and/or forensic methods. In particular, the HES levels in an individual, e.g. a patient to whom a starch (e.g., HES, e.g., VOLUVEN®) has been administered, can be readily and reliably determined shortly after administration of such a compound, thus ensuring the clinical efficacy of the compound, as well as at multiple (e.g., two or more (e.g., 2-10)) time points thereafter.

TABLE 2

Concentration in Kidney [µg equivalents/g]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 0.083 | 122974.20 | 6908.95 | | |
| 0.25 | 107349.80 | 3917.60 | | |
| 0.5 | 103092.60 | 3180.80 | 3676.20 | 2596.13 |
| 1 | 56992.65 | 1639.06 | 1774.69 | 1501.43 |
| 2 | 47729.55 | 1191.62 | | |
| 3 | | | 1023.42 | 753.91 |
| 4 | 53376.10 | 1091.12 | | |
| 6 | | | 728.30 | 694.26 |
| 7 | 50388.60 | 821.33 | | |
| 9 | | | 704.49 | 490.71 |
| 24 | | | 509.559 | 430.267 |

Figure 2:
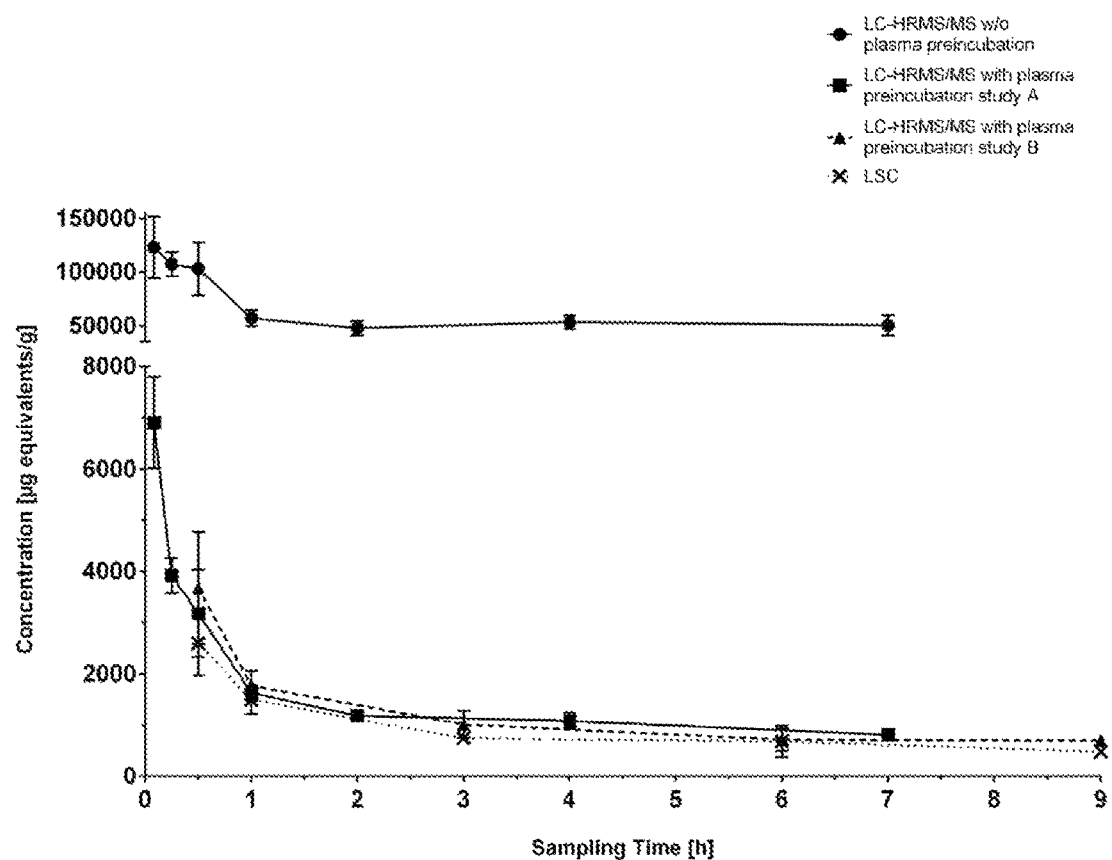
FIG. 2 is a line graph depicting the mean concentration of HES 130/0.4 (μg equivalents/ml) in tissue samples (kidney) over time (hours) as measured by LC-HRMS/MS without plasma incubation; as measured by LC-HRMS/MS with plasma incubation (study A and study B); and as measured by LSC.

The results depicted in Table 2 demonstrate that the method described above (performed in study A and study B) reliably detected the concentration of HES in kidney tissue. In particular, the measured concentrations are in accordance with those determined by LSC. Again, and in contrast to this, the omission of the incubation step leads to a significant deviation from the result obtained by LSC. These results are depicted graphically in FIG. 2.

As an excretory organ, the kidney is a tissue that is especially well suited for detecting the presence of HES in an organism.

Therefore, the present methods may especially be used in clinical and/or forensic methods, including those described above.

TABLE 3

Concentration in Lung [µg equivalents/g]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 0.083 | 29679.67 | 1553.84 | | |
| 0.25 | 22544.74 | 992.99 | | |
| 0.5 | 15878.22 | 590.68 | 860.36 | 1083.20 |
| 1 | 8632.51 | 393.51 | 628.32 | 775.57 |
| 2 | 4754.78 | 206.89 | | |
| 3 | | | 318.42 | 427.81 |
| 4 | 1379.73 | 116.14 | | |
| 6 | | | 387.74 | 268.91 |
| 7 | 1147.89 | 79.19 | | |

TABLE 3-continued

Concentration in Lung [µg equivalents/g]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 9 | | | 308.56 | 181.88 |
| 24 | | | 101.56 | 134.54 |

Figure 3:
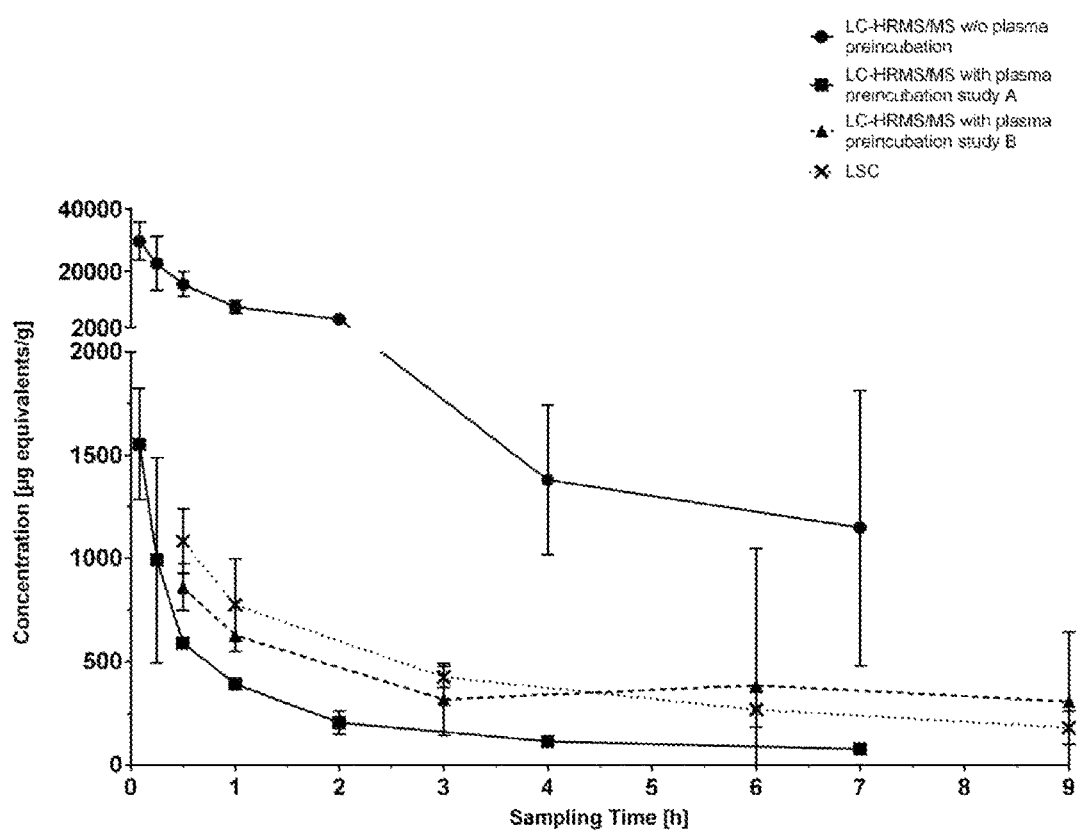
FIG. 3 is a line graph depicting the mean concentration of HES 130/0.4 (μg equivalents/ml) in tissue samples (liver) over time (hours) as measured by LC-HRMS/MS without plasma incubation; as measured by LC-HRMS/MS with plasma incubation (study A and study B); and as measured by LSC.

As with kidney tissue, the results presented in Table 3 demonstrate that the method described above (and carried out in study A and study B) also reliably detected the concentration of HES in lung tissue. Again, the measured concentrations are in accordance with those determined by LSC, while the omission of the incubation step leads to a significant deviation from the results obtained by LSC. These results are depicted graphically in FIG. 3.

Given the excellent and surprising detection results in tissue samples, the present invention may especially be used in clinical and/or forensic methods, including those described above.

TABLE 4

Concentration in Spleen [µg equivalents/g]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 0.083 | 13640.64 | 545.85 | | |
| 0.25 | 10458.92 | 399.19 | | |
| 0.5 | 7138.05 | 231.34 | 506.60 | 530.12 |
| 1 | 4216.27 | 175.77 | 349.69 | 325.01 |
| 2 | 3029.66 | 140.66 | | |
| 3 | | | 281.54 | 309.74 |
| 4 | 2405.25 | 146.17 | | |
| 6 | | | 203.52 | 248.61 |
| 7 | 2468.82 | 126.56 | | |
| 9 | | | 127.83 | 279.88 |
| 24 | | | 156.44 | 437.41 |

Figure 4:
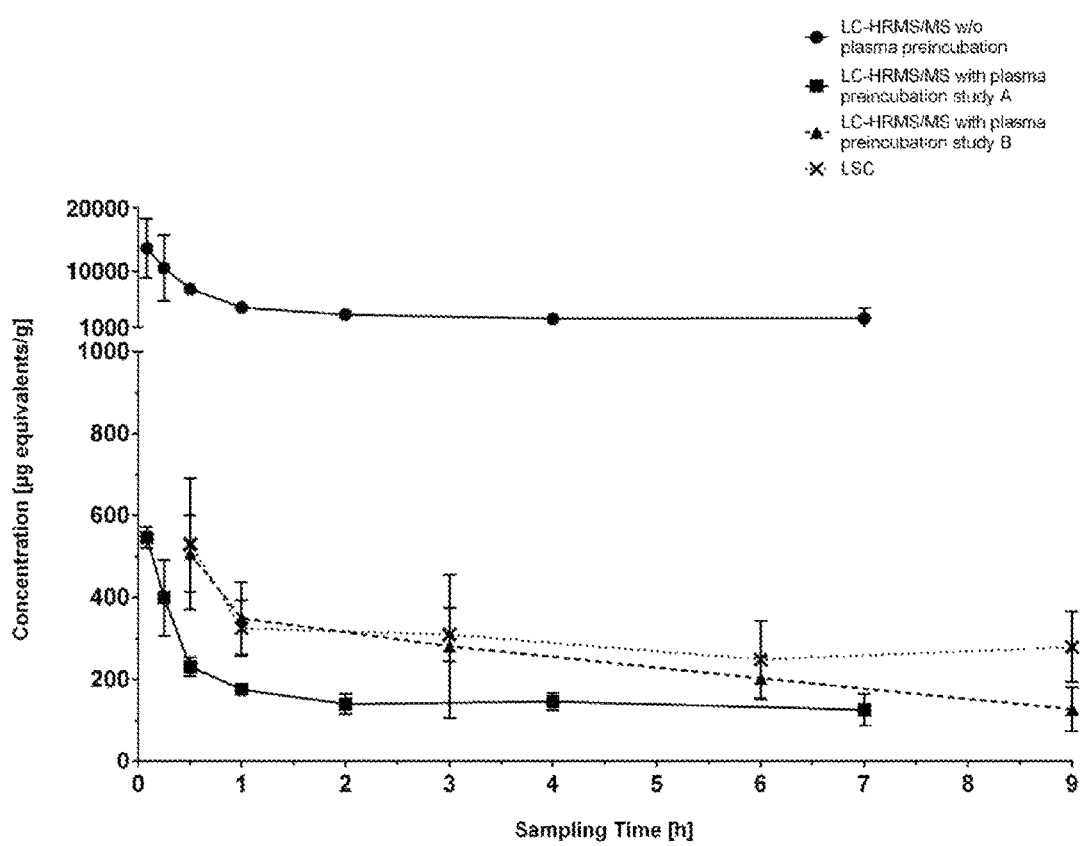
FIG. 4 is a line graph depicting the mean concentration of HES 130/0.4 (μg equivalents/ml) in tissue samples (spleen) over time (hours) as measured by LC-HRMS/MS without plasma incubation; as measured by LC-HRMS/MS with plasma incubation (study A and study B); and as measured by LSC.

The results presented in Table 4 are in accordance with the results presented in Tables 1 to 3. As with the previous samples, when a method of the present invention is carried out with a sample of spleen tissue, including an incubation step utilizing amylase, the method is superior to an analogous method omitting such an incubation step. These results are depicted graphically in FIG. 4.

Given the excellent and surprising detection results in tissue samples, the present invention may especially be used in clinical and/or forensic methods, including those described above.

TABLE 5

Concentration in Liver [µg equivalents/g]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 0.083 | 11176.80 | 896.25 | | |
| 0.25 | 8483.03 | 734.87 | | |
| 0.5 | 6643.96 | 464.24 | 570.27 | 514.90 |
| 1 | 3527.45 | 247.01 | 439.78 | 367.51 |
| 2 | 3645.59 | 223.07 | | |
| 3 | | | 346.68 | 378.94 |
| 4 | 2354.11 | 295.01 | | |

TABLE 5-continued

Concentration in Liver [μg equivalents/g]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 6 | | | 370.15 | 442.69 |
| 7 | 2932.05 | 308.84 | | |
| 9 | | | 348.52 | 448.02 |
| 24 | | | 416.93 | 486.32 |

As demonstrated by the results presented in Table 5, method according to the present invention led to a more accurate detection of HES in liver tissue than the identical method omitting the incubation step.

Furthermore, as an excretory organ, liver is a tissue that is especially well suited for detecting the presence of HES in an organism.

Given the excellent and surprising detection results in tissue samples, the present invention may especially be used in clinical and/or forensic methods, including those described above.

TABLE 6

Concentration in Bone Marrow [μg equivalents/g]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 0.083 | 5158.73 | 1850.40 | | |
| 0.25 | 5540.71 | 1076.92 | | |
| 0.5 | 2041.32 | 329.51 | 591.09 | 561.88 |
| 1 | 2348.19 | 737.86 | 304.39 | 390.34 |
| 2 | 0 | 192.83 | | |
| 3 | | | 160.39 | 228.50 |
| 4 | 0 | 182.22 | | |
| 6 | | | 108.60 | 173.81 |
| 7 | 0 | 202.53 | | |
| 9 | | | 128.65 | 144.45 |
| 24 | | | 123.18 | 133.36 |

As demonstrated by Table 6, bone marrow is also a suitable tissue sample to determine the presence (and/or concentration or amount) of HES in a subject. Likewise, the present methods led to a more accurate detection of HES in bone marrow samples than the identical method omitting the incubation step with plasma.

Given the excellent and surprising detection results in tissue samples the present invention may especially be used in clinical and/or forensic methods, including those described above.

TABLE 7

Concentration in Urine [μg equivalents/ml]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 3 | 957484.52 | 56676.16 | 52997.38 | 37832.55 |
| 6 | | | 62998.88 | 35289.32 |
| 7 | | | | |
| 9 | | | 36097.38 | 28176.07 |
| 24 | | | 34221.44 | 21251.08 |

TABLE 8

Concentration in Feces [μg equivalents/ml]

| Sampling Time [h] | LC-HRMS/MS w/o plasma preincubation | LC-HRMS/MS with plasma preincubation study A | LC-HRMS/MS with plasma preincubation study B | LSC |
|---|---|---|---|---|
| 3 | 0 | | 11941.44 | 280.99 |
| 6 | | | 6046.79 | 12586.93 |
| 7 | | | | |
| 9 | | | 4356.47 | 1886.78 |
| 24 | | | 3612.97 | 1242.39 |

Tables 7 and 8 give the results for urine and feces samples, respectively. The method according to the present invention led to a more accurate and partially more sensitive detection of HES in these samples.

Given the excellent and surprising detection results in feces and, especially, urine samples, the present methods are particularly suited for doping analysis and/or quick and reliable clinical testing.

Pharmacokinetic Evaluation

Mean pharmacokinetic parameters for various tissue types were calculated with the mean sample concentrations obtained for each sampling time point of each tissue, if possible.

TABLE 9

| | $t_{1/2}$ [h] | $AUC_{0-\infty}$ [h*μg/ml] | CL [l/h/kg] |
|---|---|---|---|
| Bone marrow | 16.85 | 6563 | 152.4 |
| Kidneys | 34.33 | 52071 | 19.2 |
| Liver | 50.00 | 30673 | 32.6 |
| Mesenteric lymph nodes | 10.08 | 8174 | 122.4 |
| Spleen | 14.45 | 7298 | 137.0 |
| Heart | 23.56 | 2462 | 406.2 |
| Urinary bladder | 5.37 | 63040 | 15.9 |
| Lung | 7.52 | 10812 | 92.5 |

$t_{1/2}$ (h): half-life within the terminal slope of a concentration-time curve; $AUC_{0-\infty}$ (μg*h/ml): area under the concentration-time curve extrapolated to infinity; CL (l/(h*kg)): total body clearance; 1 g tissue was considered as 1 ml.

The comparison of the pharmacokinetic parameters presented in Table 9 surprisingly shows that the detection of HES in tissue is an excellent means to prove the administration of HES to a subject. In particular, the detection of HES in tissue such as liver, kidney, heart, bone marrow, spleen, mesenteric lymph nodes and lung, preferably liver, kidney and heart tissue, is extremely suited to determining whether HES has been administered to a subject.

Therefore, the present invention is especially useful for reliable doping analysis and/or clinical testing, preferably in forensic applications, including those described above.

Kinetics of Amylase Digestion

In order to identify conditions of maximal HES turnover, a kinetic analysis of HES digestion by blank plasma was carried out prior to the experiments discussed above.

Blank plasma prepared with 20 IU/ml lithium heparin was spiked with HES 130/0.4 to obtain the final concentration of 4 μg HES/ml plasma. This was achieved by mixing 160 μl of blank plasma with 40 μl HES working solution (0.2 mg/ml HES 130/0.4 in EtOH/water (1+1, v/v)). 5 μl of this mixture was further diluted 1+9 with blank plasma and the samples were incubated either at room temperature or at 37° C. for 0, 60, 90, 120, 180, and 240 min.

Subsequently, all samples were processed according to the following extraction protocol: 40 μl ethanol/water (1+1, v/v; containing the processing control Griseofulvin, 1.875 ng/ml), 10 µl ethanol/water (1+1, v/v) and 50 µl TCA 27% (v/v) were added to 50 µl plasma incubate. The mixture was vigorously shaken (5 seconds) and centrifuged for 10 min at 6,000×g and 20° C. An aliquot of the particle free supernatant was transferred to an 1.5 ml sampler vial with 0.1 ml micro insert (VWR, cat. no. 5480005, 5480006, Darmstadt, Germany) and subsequently subjected to LC-HRMS.

TABLE 10

| Time [min] | HES [au] @ RT | HES [au] @ 37° C. |
|---|---|---|
| 60 | 13626 | 15055 |
| 90 | 15882 | 13731 |
| 120 | 16659 | 18744 |
| 180 |  | 15547 |
| 240 | 16380 |  | au: arbitrary units.

As can be taken from Table 10 above, a duration of the incubation in the range of 120 min yielded the best results while considerably longer durations led to a decrease in the detected amounts of starch.

Confirmation of Results with Various Starch Varieties

The determination of the detection of various other HES starches in a sub-selection of the samples mentioned above was repeated.

In particular, HES 670/0.75, HES 450/0.7, and HES 260/0.45 were detected in kidney, heart or liver tissue, while HES 200/0.62, HES 200/0.5, and HES 70/0.5 were successfully detected in urine bladder or urine with a high level of accuracy.

These results confirm that the methods of the present invention are suitable to detect a variety of starches, in particular HESs, in a variety of samples with a high sensitivity and accuracy that is comparable to the gold standard that it is dependent on radiolabeling.

With regard to the further methods and kits of the invention, it was noted above that compositions useful in detecting a starch (e.g., HES) can be used in conjunction with or packaged together with compositions useful in detecting one or more of an anabolic drug, stimulant, ergogenic aid, adaptogen, nootropic, painkiller, sedative, anxiolytic, blood booster or vectors designed for gene doping. The anabolic drug can be a drug known to build up muscle, such as a steroid, hormone (e.g., human growth hormone), a selective androgen receptor modulator, a beta-2 agonist, or prodrugs thereof; the stimulant can be a drug known to improve focus and alertness (e.g., a dopaminergic stimulant, caffeine, ephedrine, methylphenidate, and amphetamines); the ergogenic aid can be bupropion, creatine, or β-hydroxyl β-methylbutyrate; the adaptogen can be a plant product that neutralizes various environment or physical stressors; the painkiller can be any painkiller that allows performance beyond the usual pain threshold, including a non-steroidal anti-inflammatory agent such as ibuprofen or a more powerful narcotic; the sedative or anxiolytic may be diazepam or propranolol; and the blood booster may be erythropoietin (e.g., recombinant human EPO).

What is claimed is:

1. A method for detecting starch in a sample, the method comprising the steps of
    (a) incubating the sample in the presence of an amylase-containing medium; and
    (b) subjecting the sample to liquid chromatography mass spectrometry (LC-MS) to detect ions characteristic of the starch in the sample;
        wherein the amylase-containing medium comprises an amylase and blood plasma or the amylase-containing medium comprises an amylase and a component selected from the group consisting of about 90-92% water or buffered water, about 8% protein, about 0.9% salt, and/or about 1.1% organic substances;
        wherein the incubating step is done in conditions that permit digestion of the starch by the amylase.

2. The method of claim 1, wherein the sample comprises a tissue, a body fluid or feces.

3. The method of claim 1, wherein the amylase-containing medium is added to the sample prior to the incubating step.

4. The method of claim 1, wherein the starch is an artificial starch and/or HES 670/0.75, HES 450/0.7, HES 200/0.62, HES 200/0.5, HES 70/0.5, and/or HES 130/0.4.

5. The method of claim 1, wherein the ions characteristic of the starch have a mass to charge ratio (m/z) of 369, 413, and/or 575.

6. The method of claim 1, wherein the LC-MS is a high resolution tandem LC-MS (LC-HRMS/MS) with electron spray ionization (ESI) and in-source collision-induced dissociation (CID).

7. The method of claim 1, wherein the amylase is an alpha-amylase.

8. The method of claim 1, wherein the sample is incubated at a temperature of 10° C. to 50°, inclusive.

9. The method of claim 1, wherein the sample is incubated for 10 minutes to 200 minutes, inclusive.

10. The method of claim 1, wherein the sample is incubated with the amylase at a concentration of 1 to 200 U/l, inclusive.

11. The method of claim 1, wherein the incubating step occurs at room temperature for about 120 minutes, and in the presence of an α-amylase at a concentration of 4 to 20 U/l, inclusive.

12. The method of claim 1, wherein the sample is a blood sample.

13. The method of claim 1, wherein the sample is a urine sample.

14. The method of claim 1, wherein the incubating step is preceded by at least a first dilution step, wherein an amylase-containing medium is added to the sample.

15. The method of claim 14, wherein the incubating step is preceded by first and second dilution steps, wherein the second dilution step comprises the addition of an ethanol/water mixture.

16. The method of claim 1, wherein the sample in step (a) is added to said method directly after isolation from an organism and without further treatment via precipitation and/or derivation.

17. A kit comprising one or more components for detecting a starch in a sample, wherein the one or more components comprise an amylase-containing medium.

18. The kit of claim 17, wherein the amylase-containing medium comprises blood plasma.

19. The kit of claim 17, wherein the amylase-containing medium is disposed in a container to which a sample can be added.

* * * * *